(12) United States Patent
Vora et al.

(10) Patent No.: US 7,592,496 B2
(45) Date of Patent: Sep. 22, 2009

(54) LIGHT OLEFIN PRODUCTION VIA DIMETHYL ETHER

(75) Inventors: Bipin V. Vora, Naperville, IL (US); Peter R Pujado, Kildeer, IL (US)

(73) Assignee: UOP LLC, Des Plaines, IL (US)

( * ) Notice: Subject to any disclaimer, the term of this patent is extended or adjusted under 35 U.S.C. 154(b) by 545 days.

(21) Appl. No.: 11/322,897

(22) Filed: Dec. 30, 2005

(65) Prior Publication Data

US 2007/0203380 A1    Aug. 30, 2007

(51) Int. Cl.
*C07C 1/00* (2006.01)
*C07C 27/00* (2006.01)

(52) U.S. Cl. .................. 585/324; 585/639; 585/640; 518/705; 518/725

(58) Field of Classification Search ......... 585/639–640, 585/324; 518/705, 725
See application file for complete search history.

(56) References Cited

U.S. PATENT DOCUMENTS

| 5,714,662 | A | 2/1998 | Vora et al. | 585/640 |
| 5,817,906 | A * | 10/1998 | Marker et al. | 585/640 |
| 6,506,954 | B1 | 1/2003 | Brown et al. | 585/640 |
| 2004/0122267 | A1* | 6/2004 | Sher et al. | 585/324 |
| 2006/0020155 | A1* | 1/2006 | Beech et al. | 585/639 |

* cited by examiner

*Primary Examiner*—In Suk Bullock
(74) *Attorney, Agent, or Firm*—James C Paschall

(57) ABSTRACT

Improved processing for the production of light olefins is provided involving synthesis gas conversion to form an effluent including product dimethyl ether, subsequent separation of the product dimethyl ether and conversion thereof to the desired light olefins. The synthesis gas conversion effluent may also desirably include methanol and at least a portion of such methanol may be employed to effect the separation of the product dimethyl ether.

13 Claims, 1 Drawing Sheet

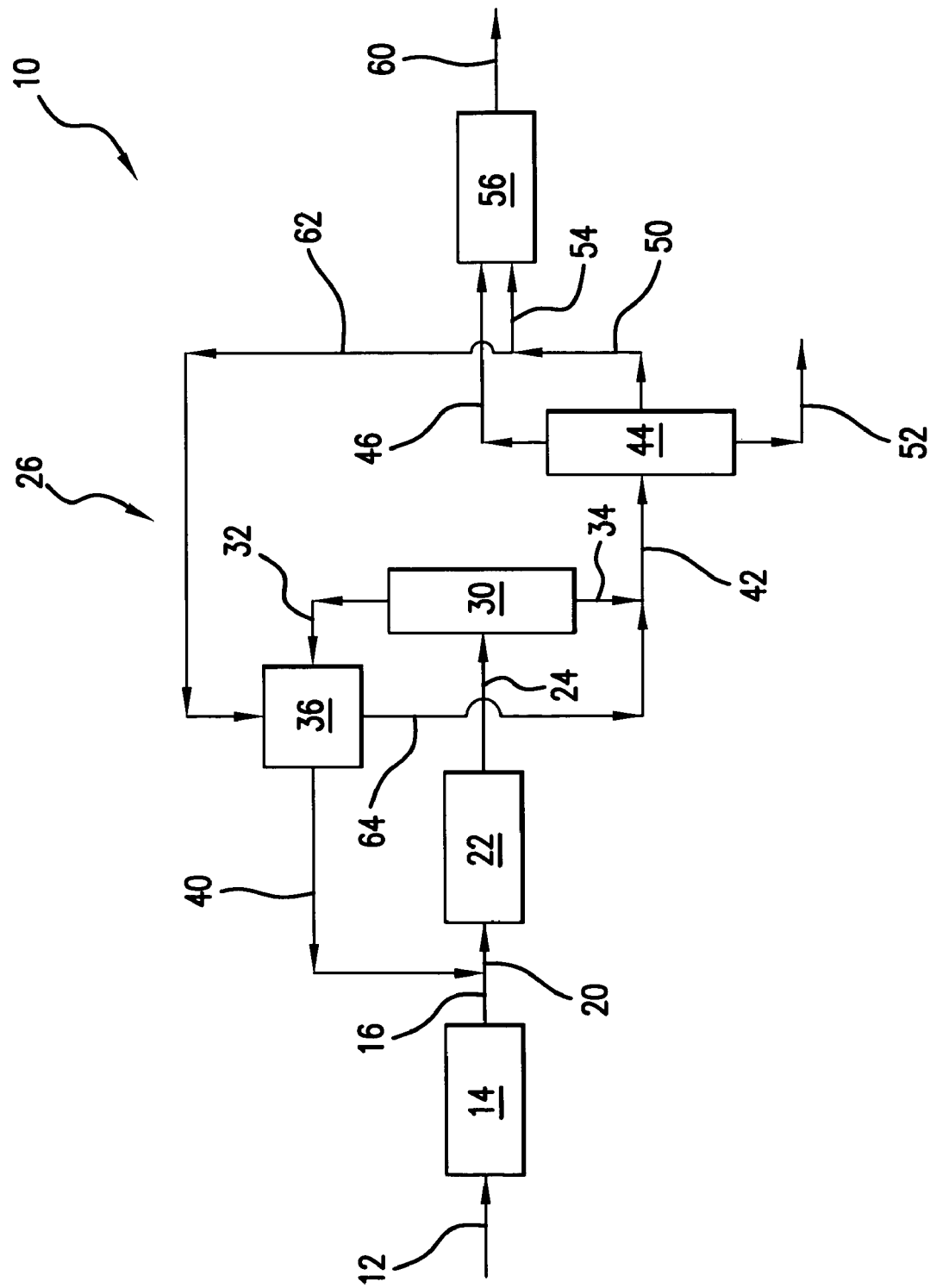

ately handle and manage the heat of reaction and byproduct
water associated with such processing.

LIGHT OLEFIN PRODUCTION VIA DIMETHYL ETHER

BACKGROUND OF THE INVENTION

This invention relates generally to the production of olefins and, more particularly, to the production of light olefins via processing of dimethyl ether.

A major portion of the worldwide petrochemical industry is concerned with the production of light olefin materials and their subsequent use in the production of numerous important chemical products such as via polymerization, oligomerization, alkylation and the like well-known chemical reactions. Light olefins generally include ethylene, propylene and mixtures thereof. These light olefins are essential building blocks used in the modern petrochemical and chemical industries. A major source for light olefins in present day refining is the steam cracking of petroleum feeds. For various reasons including geographical, economic, political and diminished supply considerations, the art has long sought sources other than petroleum for the massive quantities of raw materials that are needed to supply the demand for these light olefin materials.

The search for alternative materials for light olefin production has led to the use of oxygenates such as alcohols and, more particularly, to the use of methanol, ethanol, and higher alcohols or their derivatives such as dimethyl ether, diethyl ether, etc., for example. Molecular sieves such as microporous crystalline zeolite and non-zeolitic catalysts, particularly silicoaluminophosphates (SAPO), are known to promote the conversion of oxygenates to hydrocarbon mixtures, particularly hydrocarbon mixtures composed largely of light olefins.

Such processing, wherein the oxygenate-containing feed is primarily methanol or a methanol-water combination (including crude methanol), typically results in the release of significant quantities of water upon the sought conversion of such feeds to light olefins. For example, such processing normally involves the release of about 2 mols of water per mol of ethylene formed and the release of about 3 mols of water per mol of propylene formed. The presence of such increased relative amounts of water can significantly increase the potential for hydrothermal damage to the oxygenate conversion catalyst. Moreover, the presence of such increased relative amounts of water significantly increases the volumetric flow rate of the reactor effluent, resulting in the need for larger sized vessels and associated processing and operating equipment, including necessitating higher compression requirements.

U.S. Pat. No. 5,714,662 to Vora et al., the disclosure of which is hereby incorporated by reference in its entirety, discloses a process for the production of light olefins from a hydrocarbon gas stream by a combination of reforming, oxygenate production, and oxygenate conversion wherein a crude methanol stream (produced in the production of oxygenates and comprising methanol, light ends, and heavier alcohols) is passed directly to an oxygenate conversion zone for the production of light olefins.

While such processing has proven to be effective for light olefin production, further improvements have been desired and sought. For example, there is an ongoing desire and need for reducing the size and consequently the cost of required reaction vessels. Further, there is an ongoing desire and need for processing schemes and arrangements that can more readily handle and manage the heat of reaction and byproduct water associated with such processing.

SUMMARY OF THE INVENTION

A general object of the invention is to provide improved processing schemes and arrangements for the production of olefins, particularly light olefins.

A more specific objective of the invention is to overcome one or more of the problems described above.

The general object of the invention can be attained, at least in part, through specified methods for producing light olefins. In accordance with one embodiment, such a method involves contacting a synthesis gas-containing feedstock in a synthesis gas conversion reactor zone with a catalyst material and at reaction conditions effective to produce a synthesis gas conversion reactor zone effluent comprising product dimethyl ether, other synthesis gas conversion products (including methanol and water) and unreacted synthesis gas. Unreacted synthesis gas is separated from the product dimethyl ether and the other synthesis gas conversion products. The product dimethyl ether is separated from the other synthesis gas conversion product water and at least a portion of the other synthesis gas conversion product methanol. The method further involves contacting a feed comprising at least a portion of the separated product dimethyl ether in an oxygenate conversion reactor zone with an oxygenate conversion catalyst and at reaction conditions effective to convert the feed to an oxygenate conversion product stream comprising light olefins.

The prior art generally fails to provide processing schemes and arrangements for the production of olefins and, more particularly, to the production of light olefins from an oxygenate-containing feed and which processing schemes and arrangements are as simple, effective and/or efficient as may be desired.

A method for producing light olefins in accordance with another embodiment involves contacting a synthesis gas-containing feedstock in a synthesis gas conversion reactor zone with a catalyst material and at reaction conditions effective to convert a portion of the synthesis gas-containing feedstock to product dimethyl ether and to produce a synthesis gas conversion reactor zone effluent comprising unreacted synthesis gas, product dimethyl ether and other synthesis gas conversion products, including methanol and water. The unreacted synthesis gas and the product dimethyl ether are separated from the other synthesis gas conversion products to form a first process stream consisting essentially of the unreacted synthesis gas and the product dimethyl ether. The unreacted synthesis gas is subsequently separated from the product dimethyl ether. At least a portion of the subsequently separated unreacted synthesis gas is recycled to the synthesis gas conversion reactor zone wherein at least a portion of the recycled synthesis gas converts to product dimethyl ether. A feed comprising at least a portion of the subsequently separated product dimethyl ether is contacted in an oxygenate conversion reactor zone with an oxygenate conversion catalyst and at reaction conditions effective to convert the feed to an oxygenate conversion product stream comprising light olefins.

There is also provided a system for producing light olefins. In accordance with one preferred embodiment, such a system includes a synthesis gas conversion reactor zone for contacting a synthesis gas-containing feedstock with a catalyst material and at reaction conditions effective to convert the synthesis gas-containing feedstock to a synthesis gas conversion product stream comprising dimethyl ether, methanol unconverted synthesis gas and water. A first separator is provided for separating a vapor phase comprising unconverted synthesis gas and product dimethyl ether from a condensate phase comprising product liquid methanol and water. An absorber is provided for absorbing dimethyl ether from the vapor phase using methanol and to form a first absorber stream comprising unconverted synthesis gas and a second absorber stream comprising product dimethyl ether in methanol. A second separator is provided effective to separate product dimethyl ether from methanol in the second absorber stream. The system further includes an oxygenate conversion reactor zone for contacting a feed comprising at least a portion of the separated product dimethyl ether with an oxygenate conversion catalyst and at reaction conditions effective to convert the feed to an oxygenate conversion product stream comprising light olefins.

As used herein, references to "light olefins" are to be understood to generally refer to $C_2$ and $C_3$ olefins, i.e., ethylene and propylene. The term "carbon oxide" refers to carbon dioxide and/or carbon monoxide. The term "synthesis gas", also sometimes referred to as "syn gas", generally refers to a combination of hydrogen and carbon oxides such as produced by or in a synthesis gas production facility from a hydrocarbon gas such as derived from natural gas or from the partial oxidation of a petroleum or coal residue. Normally, synthesis gas is identified as a combination of $H_2$ and CO at various ratios, sometimes with minor amounts of $CO_2$.

Other objects and advantages will be apparent to those skilled in the art from the following detailed description taken in conjunction with the appended claims and drawing.

BRIEF DESCRIPTION OF THE DRAWING

The FIGURE is a simplified schematic diagram of a process for the production of olefins via dimethyl ether in accordance with one embodiment.

DETAILED DESCRIPTION OF THE INVENTION

A hydrocarbon gas feedstream such as a natural or synthetic natural gas stream such as produced from a natural gas, coal, shale oil, residua or combination thereof and such as typically comprises methane and ethane can be processed in a synthesis gas production facility to remove impurities such as sulfur compounds, nitrogen compounds, particulate matter, and condensibles and to provide a synthesis gas stream reduced in contaminants and containing hydrogen and carbon oxide in a desired molar ratio. Such a synthesis gas stream can in turn be introduced into a synthesis gas conversion reactor zone for contact with a catalyst material and at reaction conditions effective to produce a synthesis gas conversion reactor zone effluent that includes dimethyl ether, other synthesis gas conversion products, such as methanol and water, and unreacted synthesis gas. The synthesis gas conversion reactor zone effluent can be appropriately separated to form a stream of dimethyl ether and a stream of methanol. A feed such as generally composed of at least a portion of the separated product dimethyl ether can then be contacted in an oxygenate conversion reactor zone with an oxygenate conversion catalyst and at reaction conditions effective to convert the feed to an oxygenate conversion product stream comprising light olefins.

Reference is now made to the FIGURE which is simplified schematic process flow diagram for a process scheme, generally designated by the reference numeral 10, for the production of olefins via dimethyl ether in accordance with one embodiment. It is to be understood that no unnecessary limitation to the scope of the claims which follow is intended by the following description. Those skilled in the art and guided by the teachings herein provided will recognize and appreciate that the illustrated process flow diagram has been simplified by the elimination of various usual or customary pieces of process equipment including some heat exchangers, process control systems, pumps, fractionation systems, and the like. It may also be discerned that the process flow depicted in the FIGURE may be modified in many aspects without departing from the basic overall concept of the invention.

A hydrocarbon gas feedstream, such as described above and designated by the reference numeral 12, is passed to a synthesis gas generation or production zone 14 to produce a synthesis gas-containing stream 16. The synthesis gas generation or production zone 14, or synthesis gas production facility, can operate at conventional operating conditions such as at a reaction temperature ranging from about 800° to 950° C., a pressure ranging from about 10 to about 30 bar, and a water to carbon molar ratio ranging from about 2.0 to about 3.5. In the synthesis gas generation zone 14, impurities such as sulfur compounds, nitrogen compounds, particulate matter, and condensibles are desirably removed such as in a conventional manner to provide the synthesis gas-containing stream 16 that is reduced in contaminants and containing a molar ratio of hydrogen to carbon oxide (carbon monoxide plus carbon dioxide) ranging from about 2 to about 3, and more typically the molar ratio of hydrogen to carbon oxide varies from about 2.0 to about 2.3. Optionally (not shown), the ratio of hydrogen to carbon monoxide may be varied according to the shift reaction (1), shown below, over a copper/zinc or chromium oxide catalyst such as in a conventional manner:

$$CO+H_2O \rightarrow CO_2+H_2 \qquad (1)$$

The synthesis gas-containing stream 16 is passed via a line 20 to a synthesis gas conversion reactor zone 22. In the synthesis gas conversion reactor zone 22, at least a portion of the synthesis gas will undergo conversion to form reduction products of carbon oxides, such as alcohols, at conditions including a reactor temperature in the range of about 150° C. (300° F.) to about 450° C. (850° F.) at a pressure typically in the range of about 1 to about 1000 atmospheres over a variety of catalysts. In accordance with certain embodiments, catalysts based on ZnO for the production of methanol and dimethyl ether are preferred.

The methanol synthesis reaction can benefit from the coproduction of dimethyl ether. In particular, methanol synthesis from hydrogen gas ($H_2$) and carbon monoxide (CO) is generally equilibrium limited with typical per-pass conversion rates in the range of about 25% to about 30% at a pressure of 50 to 100 bar and a temperature in the range of about 250° to about 300° C. However, if methanol is converted to dimethyl ether, either while the methanol is being produced or shortly thereafter, the equilibrium can desirably be shifted to more favorable, higher synthesis gas conversions. As a result of such increased synthesis gas conversion rates, the amount or extent of recycle of unreacted synthesis gas, as more fully described below, can be decreased or minimized.

For example, methanol can be produced by passing synthesis gas over a supported mixed metal oxide catalyst of CuO and ZnO. Methanol conversion to dimethyl ether can be accomplished by passing such methanol over an acidic catalyst such as comprising gamma-alumina or the like. Both of the methanol formation and the methanol conversion to dimethyl ether reactions are exothermic and typically best operate at a temperature in the range of about 250° to about 300° C.

In accordance with certain preferred embodiments, the conversion of methanol to dimethyl ether can be accomplished by using a mixed catalyst system in the reactor used for methanol synthesis. In accordance with certain alternative preferred embodiments, the conversion of methanol to dimethyl ether can be accomplished by employing a reactor with alternating beds of methanol synthesis catalyst and methanol-to-dimethyl ether conversion catalyst. In accordance with certain yet other alternative preferred embodiments, the conversion of methanol to dimethyl ether can be accomplished by employing consecutive reactors for the production of methanol and subsequent conversion of methanol to dimethyl ether.

For example, a synthesis gas-containing feedstock can be contacted in a synthesis gas-to-methanol production reactor with a synthesis gas-to-methanol conversion catalyst and at reaction conditions effective to convert at least a portion of the synthesis gas-containing feedstock to a product stream comprising methanol. At least a portion of such product stream methanol can subsequently be contacted in a methanol conversion reactor with a methanol-to-dimethyl ether conversion catalyst and at reaction conditions effective to convert at least a first portion of the product stream methanol to dimethyl ether, forming the synthesis gas conversion reactor section effluent.

As will be appreciated by those skilled in the art and guided by the teaching herein provided, the reactors employed in such processing can desirably be tubular reactors with a circulating coolant, such as water, on the shell side, or adiabatic reactors such as with internal quench, interstage cooling, cooling coils or the like.

A synthesis gas conversion reactor zone effluent stream 24 comprising methanol, dimethyl ether and water is withdrawn from the synthesis gas conversion reactor zone 22.

The synthesis gas conversion reactor zone effluent stream 24, such as after cooling such as via one or more heat exchangers (not shown) is passed to a separation zone, generally designated by the reference numeral 26. The separation zone 26 includes a first separation section 30, such as generally composed of a flash system, fractionator, or a stripper for the removal of unconverted synthesis gas, followed by similar means for the consecutive separation of dimethyl ether, methanol, and water fractions as may be required or desired by the downstream operation.

For example, in accordance with one preferred embodiment, the separation realized in such a first separation section can be in the form of a partial condensation separation with unreacted synthesis gas and a portion of the product dimethyl ether being separated from the other synthesis gas conversion products (e.g., methanol, water and some dimethyl ether) such as to form a first or overhead process stream 32 such as generally composed of unreacted synthesis gas and product dimethyl ether and, in accordance with certain preferred embodiments, consisting essentially of unreacted synthesis gas and product dimethyl ether, and a lower or bottoms stream 34 such as generally composed of methanol, water and some product dimethyl ether.

As described in greater detail below, the first or overhead process stream 32 can be forwarded to an appropriate dimethyl ether-synthesis gas separation section 36. The dimethyl ether-synthesis gas separation section 36 desirably results in or produces a stream 40 such as generally containing unreacted synthesis gas and such as can desirably be introduced into, e.g., recycled to, the synthesis gas conversion reactor zone 22 via the above-identified line 20 for subsequent reaction.

The bottoms stream 34 of methanol, water and some product dimethyl ether can be sent via the line 42 to a second separation section 44, such as in the form of a dimethyl ether stripper, such as generally composed of a fractionator for the separation of lighter and heavier components, with dimethyl ether being relatively lighter than methanol and methanol being relatively lighter than water and other heavy impurities or byproducts (e.g., heavy alcohols).

In the second separation section 44, product dimethyl ether can be separated from other feed constituents such as to form a stream 46 comprising dimethyl ether. In addition, a side stream 50 such as generally composed of methanol can be formed. Further, a bottoms stream 52 such as composed of water and heavy impurities or byproducts (e.g., heavy alcohols). Such a bottom stream can be further treated for the removal of such heavy impurities and byproducts and the water can, if desired, be recycled to the synthesis gas generation unit or, alternatively utilized such as in irrigation or other agricultural uses.

As shown, at least a portion of the dimethyl ether from the stream 46 and, if desired, at least a portion of the methanol from the stream 50, as signified by the line 54, can be introduced into an oxygenate conversion reactor zone 56 wherein such oxygenate-containing feedstock materials contact with an oxygenate conversion catalyst at reaction conditions effective to convert the oxygenate-containing feedstock to form an oxygenate conversion effluent stream comprising fuel gas hydrocarbons, light olefins, and $C_{4+}$ hydrocarbons, in a manner as is known in the art, such as, for example, utilizing a fluidized bed reactor.

In accordance with preferred embodiment, the feed to the oxygenate conversion reactor zone 56 desirably comprises 70 to 90 mol-% separated product dimethyl ether and 10 to 30 mol-% methanol. Those skilled in the art and guided by the teachings herein provided will understand and appreciate that the relative ratios of dimethyl ether, methanol, and water can generally vary dependent on factors such as the operating conditions used in the conversion of methanol to dimethyl ether and the separation steps used thereafter. For example, if starting with a stream that contains 100 mols of methanol and 30 mols of water (about 77 mol-% methanol) and then converting this stream to dimethyl ether at equilibrium over an acidic catalyst (e.g., gamma alumina) at 250° C., a product alternatively comprising, consisting essentially of, or consisting of approximately of 43.3 mols of dimethyl ether, 73.3 mols of water, and 13.5 mols of residual unconverted methanol is obtained. If only water is removed, the final product will contain about 76.3 mol-% dimethyl ether in a mixture with 23.7 mol-% methanol. While no further separation of dimethyl ether and methanol is necessary, it may be desirable to further separate the dimethyl ether from the methanol (to obtain up to close to 100 mol-% dimethyl ether purity) in order to minimize hydrothermal effects on the oxygenate-to-olefin conversion catalyst; in such an event, the methanol thus separated can desirably be recycled to the methanol-to-dimethyl ether conversion stage.

Reaction conditions for the conversion of oxygenates to light olefins are known to those skilled in the art. Preferably, in accordance with particular embodiments, reaction conditions comprise a temperature between about 200° and about 700° C., more preferably between about 300° and 600° C., and most preferably between about 400° and about 550° C. As will be appreciated by those skilled in the art and guided by the teachings herein provided, the reaction conditions are generally variable such as dependent on the desired products. For example, if increased ethylene production is desired, then operation at a reactor temperature between about 475° and about 550° C. and more preferably between about 500° and about 520° C., may be preferred. If increased propylene production is desired, then operation at a reactor temperature between about 350° and about 475° C. and more preferably between about 400° and about 430° C. may be preferred. The light olefins produced can have a ratio of ethylene to propylene of between about 0.5 and about 2.0 and preferably between about 0.75 and about 1.25. If a higher ratio of ethylene to propylene is desired, then the reaction temperature is generally desirably higher than if a lower ratio of ethylene to propylene is desired. In accordance with one preferred embodiment, a feed temperature range between about 120° and about 210° C. is preferred. In accordance with another preferred embodiment a feed temperature range of between about 180° and 210° C. is preferred. In accordance with one preferred embodiment, the temperature is desirably maintained below 210° C. to avoid or minimize coking on associated processing equipment such as feed heaters and vaporizers.

The oxygenate conversion reactor zone 56 produces or results in an oxygenate conversion product or effluent stream 60 such as generally comprising fuel gas hydrocarbons, light olefins, and $C_{4+}$ hydrocarbons. The oxygenate conversion effluent stream 60 can, if desired, be passed to an oxygenate conversion effluent stream treatment zone (not shown) such as known in the art for the appropriate desired product separation and recovery of and from such effluent stream.

The balance of the methanol from the stream 50, signified by the stream 62, is forwarded to the dimethyl ether-synthesis gas separation zone 36 such as described above and such as in the form of an absorber.

In such a dimethyl ether-synthesis gas separation zone absorber, methanol is desirably employed as a solvent to absorb dimethyl ether from the unreacted synthesis gas such as to form the above-identified unreacted synthesis gas recycle stream 40 and also desirably results in or produces a stream 64 such as generally containing dimethyl ether and methanol. Moreover, such embodiment desirably employs internally generated methanol to effect such absorption of dimethyl ether. The dimethyl ether and methanol-containing stream 64 can desirably subsequently be introduced into the second separation section 44 such as via the line 42.

As a result of such selective absorption of dimethyl ether using methanol, the unreacted synthesis gas recycle stream 40 will desirably be substantially free of dimethyl ether. More specifically, the unreacted synthesis gas recycle stream 40 will generally contain less than 1000 ppm of dimethyl ether and, in accordance with a preferred embodiment, less than 100 ppm of dimethyl ether. Thus, through such application of methanol absorption of dimethyl ether, the undesirable recycling of dimethyl ether through the synthesis gas conversion reactor zone 22 can be minimized or avoided, such as to increase or improve processing efficiency. Moreover, by avoiding or minimizing the amount of dimethyl ether recycled to the synthesis gas conversion reactor zone 22, the equilibrium reaction between methanol and dimethyl ether can desirably be driven, in accordance with a preferred embodiment, towards the production of additional, increased or further relative amounts of dimethyl ether.

As will be appreciated, with such recycle of unreacted synthesis gas, at least a portion of the synthesis gas unreacted on its initial pass through the synthesis gas conversion reactor zone 22 can react such as to form additional synthesis gas conversion reactor zone products including additional product dimethyl ether and such as can be appropriately processed through the subject process scheme, such as described above.

The present invention is described in further detail in connection with the following examples which illustrate or simulate various aspects involved in the practice of the invention. It is to be understood that all changes that come within the spirit of the invention are desired to be protected and thus the invention is not to be construed as limited by these examples.

EXAMPLES

Those skilled in the art and guided by the teachings herein provided will appreciate that the use of dimethyl ether as a primary or principal oxygenate feedstock to such an oxygenate conversion reactor section and, in accordance with certain preferred embodiments, and excluding residual amounts of other materials, as the primary or principal oxygenate feedstock and, in accordance with other certain preferred embodiments and excluding residual amounts of other materials, as the sole oxygenate feedstock, desirably produces or results in various processing advantages.

Example 1

Reactor Size

Methanol conversion to the light olefins ethylene and propylene at a 1:1 weight ratio necessitates the following processing reaction:

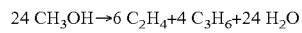

$$24\ CH_3OH \rightarrow 6\ C_2H_4 + 4\ C_3H_6 + 24\ H_2O$$

In such processing, 24 mols of methanol feed becomes 34 mols of product effluent. The use of dimethyl ether, in accordance with a preferred embodiment, for a similar conversion to the light olefins ethylene and propylene at a 1:1 weight ratio necessitates the following processing reaction:

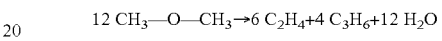

$$12\ CH_3\text{---}O\text{---}CH_3 \rightarrow 6\ C_2H_4 + 4\ C_3H_6 + 12\ H_2O$$

In such processing, 12 mols of dimethyl ether feed becomes 22 mols of product effluent.

Thus, processing in accordance with the above reaction from dimethyl ether as opposed to reaction from methanol, both for the same number of mols of ethylene and propylene, results in a reduced number of mols of effluent (e.g., 22 mols versus 34 mols). Such reduction in the number of mols represents an equivalent reduction in the volumetric flow rate of effluent from the reactor, and thus a smaller reactor vessel, and also lower compression requirements of such effluent to downstream separation units. Moreover, as such a reduction in moles is accomplished by reducing the mols of water, the partial pressure of water is reduced from 70.6% (24/34) to 54.5% (12/22) in relative units. Such reduction in the relative amount of water can desirably result in improving the stability of the catalyst used in the conversion of oxygenates to light olefins Example 2

Heat of Reaction

The heat of reaction, at 450° C., for the oxygenate conversion reaction of two mols of methanol to one mol of ethylene (plus water) is about 5.5 kcal/mol. In contrast, for the conversion of one mol of dimethyl ether to one mol of ethylene (plus water) in accordance with one preferred embodiment, the heat of reaction is only about 0.8 kcal/mol.

Those skilled in the art will appreciate that such a significant reduction in the heat of reaction can dramatically simplify and facilitate management of the adiabatic temperature rise realized within the oxygenate conversion reactor upon such reaction. Thus, in accordance with certain preferred embodiments, the oxygenate conversion reactor can desirably be free of cooling devices such as cooling coils an/or catalyst coolers, such as may typically be required in such oxygenate-to-olefin conversion reactors.

Embodiments, such as described above, incorporating and utilizing synthesis gas conversion to form an effluent including product dimethyl ether, subsequent separation of such product dimethyl ether and conversion thereof to form light olefins desirably provides or results in improved processing such as by minimizing or at least reducing the size of required vessels.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A method for producing light olefins, said method comprising:
   contacting a synthesis gas-containing feedstock in a synthesis gas conversion reactor zone with a catalyst material and at reaction conditions effective to produce a synthesis gas conversion reactor zone effluent comprising product dimethyl ether, other synthesis gas conversion products and unreacted synthesis gas, the other synthesis gas conversion products comprising methanol and water;
   separating the unreacted unreacted synthesis gas and the product dimethyl ether from the other synthesis gas conversion products methanol and water to form a first process stream comprising the synthesis gas and product dimethyl ether;
   separating the other synthesis gas conversion product methanol from the other synthesis gas conversion product water;
   contacting the first process stream with at least a portion of the separated product methanol in a separation vessel to separate the product dimethyl ether from the unreacted synthesis gas by absorbing the product dimethyl ether into the separated product methanol; and
   contacting a feed comprising at least a portion of the separated product dimethyl ether in an oxygenate conversion reactor zone with an oxygenate conversion catalyst and at reaction conditions effective to convert the feed to an oxygenate conversion product stream comprising light olefins.

2. The method of claim 1 additionally comprising recycling at least a portion of the separated unreacted synthesis gas to the synthesis gas conversion reactor zone wherein at least a portion of the recycled synthesis gas converts to product dimethyl ether.

3. The method of claim 1 wherein the feed to the oxygenate conversion reactor zone comprises at least about 70 mol-% separated product dimethyl ether.

4. The method of claim 1 wherein the separation of the unreacted synthesis gas from the product dimethyl ether and the other synthesis gas conversion products forms an unreacted synthesis gas stream substantially free of dimethyl ether.

5. The method of claim 4 additionally comprising recycling the unreacted synthesis gas stream to the synthesis gas conversion reactor zone.

6. The method of claim 1 wherein at least a portion of the product dimethyl ether is separated from the separated product methanol.

7. The method of claim 1 wherein the feed to the oxygenate conversion reactor zone comprises 70 to 90 mol-% separated product dimethyl ether and 10 to 30 mol-% methanol.

8. The method of claim 1 wherein the contacting of the synthesis gas-containing feedstock in a synthesis gas conversion reactor zone with a catalyst material and at reaction conditions effective to produce a synthesis gas conversion reactor zone effluent comprises:
   contacting the synthesis gas-containing feedstock in a synthesis gas-to-methanol production reactor zone with a synthesis gas-to-methanol conversion catalyst and at reaction conditions effective to convert at least a portion of the synthesis gas-containing feedstock to a product stream comprising methanol; and
   contacting at least a portion of the product stream methanol in a methanol conversion reactor zone with a methanol-to-dimethyl ether conversion catalyst and at reaction conditions effective to convert at least a first portion of the product stream methanol to dimethyl ether, forming the synthesis gas conversion reactor section effluent.

9. The method of claim 8 wherein the synthesis gas-to-methanol production reactor zone and the methanol conversion reactor zone comprise a single reactor containing a mixed catalyst.

10. The method of claim 8 wherein the synthesis gas-to-methanol production reactor zone and the methanol conversion reactor comprise alternating beds of methanol synthesis catalyst and methanol-to-dimethyl ether conversion catalyst.

11. A method for producing light olefins, said method comprising:
    contacting a synthesis gas-containing feedstock in a synthesis gas conversion reactor zone with a catalyst material and at reaction conditions effective to convert a portion of the synthesis gas-containing feedstock to product dimethyl ether and to produce a synthesis gas conversion reactor zone effluent comprising unreacted synthesis gas, product dimethyl ether and other synthesis gas conversion products, the other synthesis gas conversion products comprising methanol and water;
    separating the unreacted synthesis gas and the product dimethyl ether from the other synthesis gas conversion products to form a first process stream consisting essentially of the unreacted synthesis gas and the product dimethyl ether;
    separating the other synthesis gas conversion product methanol from the other synthesis gas conversion product water;
    contacting the first process stream with at least a portion of the separated product methanol in a separation vessel to separate the product dimethyl ether from the unreacted synthesis gas by absorbing the product dimethyl ether into the separated product methanol;
    recycling at least a portion of the subsequently separated unreacted synthesis gas to the synthesis gas conversion reactor zone wherein at least a portion of the recycled synthesis gas converts to product dimethyl ether; and
    contacting a feed comprising at least a portion of the subsequently separated product dimethyl ether in an oxygenate conversion reactor zone with an oxygenate conversion catalyst and at reaction conditions effective to convert the feed to an oxygenate conversion product stream comprising light olefins.

12. The method of claim 11 wherein the feed to the oxygenate conversion reactor zone comprises 70 to 90 mol-% separated product dimethyl ether and 10 to 30 mol-% methanol.

13. The method of claim 11 wherein the feed to the oxygenate conversion reactor zone comprises at least about 70 mol-% separated product dimethyl ether.

* * * * *

UNITED STATES PATENT AND TRADEMARK OFFICE
CERTIFICATE OF CORRECTION

PATENT NO. : 7,592,496 B2  Page 1 of 1
APPLICATION NO. : 11/322897
DATED : September 22, 2009
INVENTOR(S) : Bipin V. Vora et al.

It is certified that error appears in the above-identified patent and that said Letters Patent is hereby corrected as shown below:

Column 9,

Claim 1, line 19, replace "separating the unreacted unreacted synthesis gas" with --separating the unreacted synthesis gas--.

Claim 1, line 22, replace "process stream comprising the synthesis gas" with --process stream comprising the unreacted synthesis gas--.

Signed and Sealed this

Tenth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,592,496 B2 Page 1 of 1
APPLICATION NO. : 11/322897
DATED : September 22, 2009
INVENTOR(S) : Vora et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 806 days.

Signed and Sealed this

Twenty-first Day of September, 2010

David J. Kappos
*Director of the United States Patent and Trademark Office*